US007666847B2

(12) United States Patent
Houlmont et al.

(10) Patent No.: US 7,666,847 B2
(45) Date of Patent: Feb. 23, 2010

(54) MEDICAMENT COMPRISING A REDUCING ALKYL-SUGAR MONOMER FOR THE TREATMENT OF INFLAMMATORY DISORDERS

(75) Inventors: Jean-Philippe Houlmont, Ramonville Saint-Agne (FR); Isabelle Rico-Lattes, Auzielle (FR); Emile Perez, Colomiers (FR); Pascal Bordat, Mervilla (FR)

(73) Assignees: Pierre Fabre Dermo-Cosmetique, Boulogne-Billancourt (FR); Centre National de la Recherche Scientifique (CNRS), Paris (FR)

( * ) Notice: Subject to any disclaimer, the term of this patent is extended or adjusted under 35 U.S.C. 154(b) by 427 days.

(21) Appl. No.: 10/577,444

(22) PCT Filed: Oct. 29, 2004

(86) PCT No.: PCT/FR2004/002794

§ 371 (c)(1),
(2), (4) Date: Apr. 27, 2006

(87) PCT Pub. No.: WO2005/041983

PCT Pub. Date: May 12, 2005

(65) Prior Publication Data

US 2007/0134187 A1 Jun. 14, 2007

(30) Foreign Application Priority Data

Oct. 31, 2003 (FR) .................................. 03 12798

(51) Int. Cl.
*A61K 31/7028* (2006.01)
*C07G 3/00* (2006.01)

(52) U.S. Cl. .......................................... 514/25; 536/4.1
(58) Field of Classification Search ....................... None
See application file for complete search history.

(56) References Cited

U.S. PATENT DOCUMENTS

2004/0136938 A1  7/2004  Ladislas et al.

FOREIGN PATENT DOCUMENTS

| DE | 197 04 693 A1 | 8/1998 |
| DE | 19845271 A1 * | 6/2000 |
| EP | 0 804 923 A2 | 5/1997 |
| EP | 0 804 924 A2 | 5/1997 |
| FR | 2 652 742 A | 4/1991 |
| FR | 2 756 735 A | 6/1998 |
| FR | 2 768 623 A | 3/1999 |
| FR | 2 813 789 A | 3/2002 |
| JP | 2004168666 | 6/2004 |
| WO | WO-96 29339 A1 | 9/1996 |
| WO | WO-2004/006959 A1 | 1/2004 |

OTHER PUBLICATIONS

Machine translation of DE19845271, translated by ep.espacenet.com.*
Merriam-Webster's Collegiate Dictionary, Tenth Edition, published 1998 by Merriam-Webster, Incorporated, p. 924.*
Jefferies, Ian et al.; Bio & Med. Chem.Letters, vol. 7, No. 9, pp. 1171-1174 (1997).
Niu, X. et al., FASEB Journal, Data base XP009081815; Annual Meeting of FASEB; (Mar. 2001); Abstract No. 687.4.
Banaszek, Anna; Carbohydrate Research, vol. 306, pp. 379-385 (1998).
Houlmont, J.-P.; International Journal of Cosmetic Science, No. 23, pp. 363-368 (2001).
Liao, J.-H. et al.; Organic Letters, vol. 4, No. 18, pp. 3107-3110 (2002).
Lowary, Todd L. et al.; Carbohydrate Research, vol. 256, pp. 257-273 (1994).
Pathak, A. K. et al.; Bioorganic and Medicinal Chemistry, vol. 7, pp. 2407-2413 (1999).
Schweiger, Richard G.; Journal of Chemical and Engineering Data, vol. 9, No. 3, pp. 408-410 (1964).
Tane, Pierre; Tetrahedron Letters, vol. 29, No. 15, pp. 1837-1840 (1988).
Vermeer, H. J. et al.; European Journal of Organic Chemistry, pp. 193-203 (2001).
Vill, V. et al.; Chemistry and Physics of Lipids; No. 104, pp. 75-91 (2000).
M. Schmidt et al., Chemistry and Physics of Lipids, vol. 114, 2002, pp. 139-147.

* cited by examiner

*Primary Examiner*—Shaojia Anna Jiang
*Assistant Examiner*—Eric S Olson
(74) *Attorney, Agent, or Firm*—Birch, Stewart, Kolasch & Birch, LLP.

(57) ABSTRACT

The invention relates to a medicament comprising at least one reducing alkyl-sugar monomer having a hydroxyl function which is substituted by an alkoxy radical at $C_2$-$C_{40}$, said medicament being preferably intended to regulate inflammatory mechanisms. The reducing sugar is preferably selected from the group containing rhamnose, fucose and glucose. The invention also relates to a cosmetic treatment method involving the topical application of a composition comprising at least one reducing alkyl-sugar monomer having a hydroxyl function which is substituted by an alkoxy radical at $C_2$-$C_{40}$.

14 Claims, 2 Drawing Sheets

Figure 1:
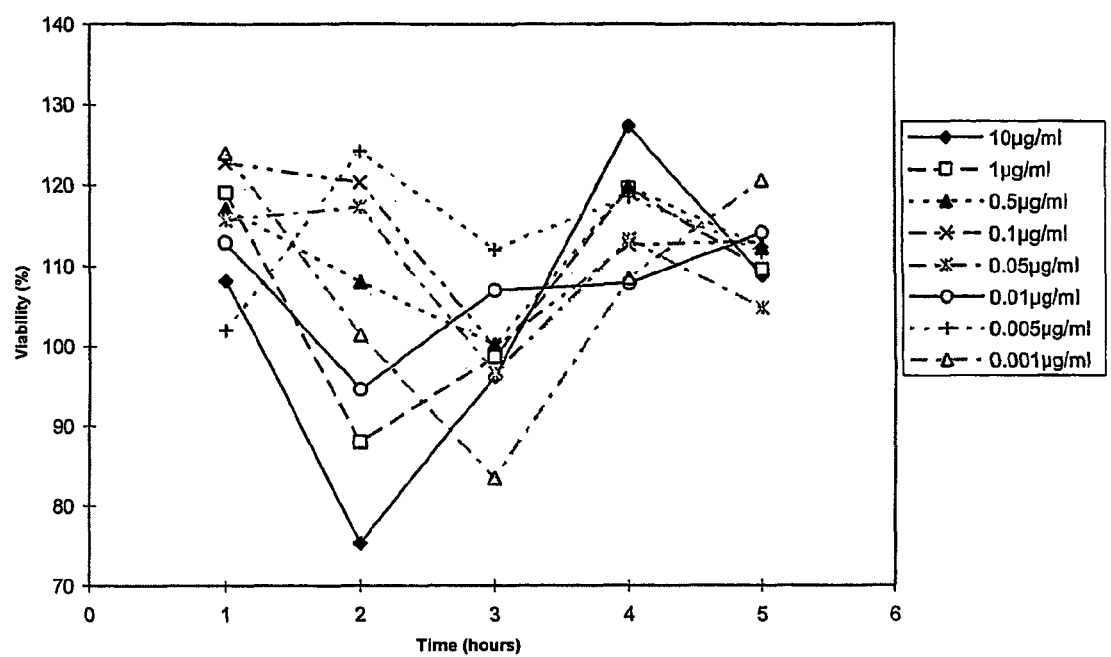

MEDICAMENT COMPRISING A REDUCING ALKYL-SUGAR MONOMER FOR THE TREATMENT OF INFLAMMATORY DISORDERS

The present invention relates to novel reducing alkyl-sugar monomers as well as the use thereof as medicaments, in particular as anti-inflammatory agents.

The inflammatory reaction is a response by the immune system of an organism faced with an attack against its cells or vascularized tissues by a pathogen such as a virus or a bacterium, or by a chemical or physical attack. Often painful, inflammation is generally a healing response. In certain cases, however, (rheumatoid arthritis, Crohn's disease, autoimmune diseases, etc.) it can have consequences more serious than the original stimulus.

Contact hypersensitivity reactions correspond to specific immunity reactions directed against antigens located on cells or in tissues, at the origin of cellular lesions or inflammatory reactions. These hypersensitivity reactions can develop within the framework of defense mechanisms with respect to a pathogenic microorganism or in the case of allergic reactions. They utilize various types of cells, in particular skin cells and certain leucocytes, not to mention endothelial cells whose role is preponderant in inflammatory reactions.

The intercellular interactions which intervene generally imply specific recognition phenomena between ligands and receptors. During the past twenty years, many cellular surface receptors have been identified, such as proteins capable of ensuring specific recognition with certain sugars such as fucose and rhamnose.

Lectins are proteins imbedded in the membranes of eukaryotic cells which play a very important role in adhesion and recognition phenomena between cells, in particular during inflammatory processes. Membrane lectins are implicated in particular in endocytosis, intracellular transport of glycoconjugates and endothelial permeability. Moreover, these proteins, often transmembrane proteins, contribute to specific antigen recognition (extracellular domain) and to cell activation (intracellular domain). Lectins can specifically recognize certain sugars, in particular rhamnose.

For a number of years, alkyl polysaccharides ($C_mG_n$, where m is the number of carbons in the alkyl chain and n the number of glycoside units composing the hydrophilic head) have constituted an interesting family of nonionic surfactants. For example, alkyl polyglucosides (APGs), which are prepared industrially from glucose and fatty alcohol, find a number of applications in detergency and in addition in beauty care due to their satisfactory dermatological tolerance.

The publication "Cosmetic use formulation containing pentyl rhamnoside and cetyl rhamnoside," J. P. Houlmont et al., International Journal of Cosmetic Science, 2001, 23, 363-368, describes the synthesis and use of pentyl and cetyl rhamnoside as a co-surfactant and surfactant, respectively, as well as their adequacy for cosmetic formulations. These alkyl rhamnosides (at $C_5$ and $C_{16}$) are produced directly by the acetylation of L-rhamnose in a suitable alcohol in the presence of an acid catalyst. These alkyl rhamnosides are described as being biocompatible and not very toxic.

The patent application EP 0804923 describes a composition comprised of a polysaccharide alkyl ether which includes at least two different sugar units and at least one hydroxyl group substituted by a saturated alkyl chain at $C_1$-$C_{24}$. This composition makes it possible to protect the skin from ultraviolet radiation.

The patent application EP 0804924 describes a composition intended to prolong the longevity of a perfume on the skin which includes at least one polysaccharide alkyl ether comprised of at least two different sugar units and at least one hydroxyl group substituted by a saturated alkyl chain at $C_1$-$C_{24}$.

The present invention relates to monomers of alkyl-rhamnose or of alkyl-fucose of formula I:

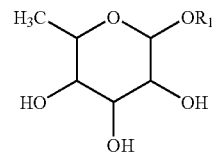

in which $R_1$ represents an alkyl radical at $C_2$-$C_{40}$, preferably at $C_2$-$C_{24}$, including all the isomer forms thereof, with the exception of products of formulas

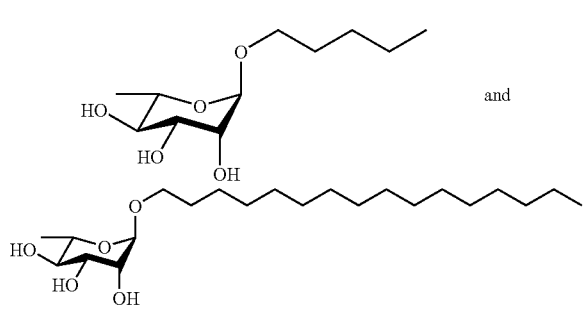

and $R_1$ advantageously represents an alkyl radical at $C_5$-$C_{12}$, preferably at $C_5$-$C_8$.

According to an advantageous variant of the invention, $R_1$ represents a radical chosen from the group comprised of pentyl, octyl, decyl and undecyl.

Within the framework of the present invention, "alkyl-rhamnose monomer" is used interchangeably with "alkyl-rhamnoside," and "alkyl-fucose monomer" is used interchangeably with "alkyl-fucoside."

The rhamnose or fucose can be levorotatory of or dextrorotatory configuration. According to an advantageous variant of the invention, the rhamnose or fucose is of levorotatory configuration.

The rhamnose or fucose can be in α- or β-anomeric form. According to another advantageous variant of the invention, the rhamnose or fucose is in the α-anomeric form.

The present invention also relates to a medicament comprised of at least one reducing-sugar monomer whose hydroxyl function, advantageously the anomeric hydroxyl function, is substituted by an alkoxy radical at $C_2$-$C_{40}$, preferably at $C_2$-$C_{24}$. Within the framework of the present invention, these reducing-sugar monomers whose hydroxyl function is substituted by an alkoxy radical are called reducing alkyl-sugars. Reducing alkyl-sugars are of the following general formula:

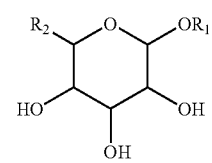

in which $R_2$ represents the radical —$CH_3$ or the radical —$CH_2OH$ and $R_1$ represents an alkyl radical at $C_2$-$C_{40}$, preferably at $C_2$-$C_{24}$.

Within the context of the present invention, a "reducing sugar" is understood to mean a sugar that exhibits, when it is in linear form, a free aldehyde function carried by the carbon anomer. Reducing sugars can be demonstrated in a solution with Fehling's test for reducing sugars. As examples of reducing sugars, glucose, fructose, maltose, galactose and lactose can be cited in particular.

Within the framework of the present invention, the reducing sugar is advantageously selected from the group comprised of rhamnose, fucose and glucose.

The rhamnose, fucose or glucose can be of a levorotatory or dextrorotatory configuration. According to an advantageous variant of the invention, the rhamnose, fucose or glucose is of a levorotatory configuration.

The rhamnose, fucose or glucose can be in the α- or β-anomeric form. According to another advantageous variant of the invention, the rhamnose, fucose or glucose is in the α-anomeric form.

According to an advantageous variant of the invention, the alkoxy radical includes from 5 to 12 carbon atoms, preferably 5 to 8 carbon atoms. Thus, $R_1$ advantageously represents an alkyl radical at $C_5$-$C_{12}$, preferably at $C_5$-$C_8$. According to an advantageous variant of the invention, $R_1$ represents a radical chosen from the group comprised of pentyl, octyl, decyl and undecyl.

The invention is characterized by the fact that the reducing sugar, carrying an alkyl radical, is exclusively in monomeric form.

The aforementioned reducing alkyl-sugar monomers, in particular the alkyl-rhamnose, alkyl-fucose or alkyl-glucose monomers according to the invention, can be synthesized in a single-step reaction, without any step of protection or deprotection of the hydroxyl functions of the reducing sugar, by a condensation reaction of the reducing sugar, in particular the rhamnose, fucose or glucose, with an alcohol, having a number of atoms corresponding to the length of the alkyl chain.

The synthesis process used is a standard Fischer reaction with p-toluenesulfonic acid (PTSA) as the acid catalyst. It is carried out in a "one-pot" manner: the reagents (reducing sugar, in particular rhamnose, fucose or glucose, alcohol, and acid catalyst) are placed together without using solvent, and thus the medium is in heterogeneous form.

The reducing-sugar mixture, in particular rhamnose, fucose or glucose, alcohol and acid catalyst, is advantageously brought into reaction under heating and possibly under stirring at a temperature between 20° C. and 120° C., even more advantageously between 35° C. and 75° C. The temperature should not be too high, in particular it should not exceed 120° C., in order to avoid degradation of the sugars. The mixture is advantageously mixed for between 5 minutes to 24 hours, still more advantageously for 3 hours.

The anomeric function being the most reactive, by virtue of the stabilization of the carbocation by resonance, the alcohol is added exclusively at position 1.

The alcohol, in excess, in a molar ratio approximately double compared to the reducing sugar, in particular to the rhamnose, fucose or glucose, is used as a solvent in the synthesis product, and thus the reaction medium is in a homogeneous phase at the end of the reaction. A relatively strong Bronsted acid that is soluble in an organic medium, such as PTSA, is chosen as the acid catalyst. Sulfuric acid that is too strong and hydrochloric acid thus could not be used because they are water soluble, whereas carboxylic acids are not strong enough. It is necessary to avoid working in the presence of water, because water further favors the reverse hydrolysis reaction rather than the addition reaction.

The self-condensation of the reducing-sugar monomers, in particular of alkyl-rhamnose, alkyl-fucose or alkyl-glucose, is limited or even eliminated, although each hydroxyl function, from a theoretical point of view, is capable of reacting with another to create a glycoside bond and thus increasing the degree of polymerization, because of the absence of protective agents. It is supposed that this self-condensation is eliminated because the 6-deoxy sugars (rhamnose, fucose in particular) lack a primary hydroxyl function and have a methyl group in its place. The methyl group of the 6-deoxy sugars would favor alkyl-monosaccharide formation by eliminating a highly-reactive hydroxyl function carried by carbon 6 and by adding a steric problem in the vicinity of carbon 4.

For all of the reducing alkyl-sugars, this synthesis leads to the α-anomer configuration in which the steric problem is minimized and which is thus the most thermodynamically stable. In particular, for the majority of the alkyl-rhamnosides, this synthesis leads to the α-anomer. The α/β anomeric ratio for the alkyl-fucosides is near 2.

According to an advantageous variant of the invention, the water formed during the condensation reaction is eliminated, physically or chemically. As an example of a physical technique for eliminating the water formed during the synthesis, distillation or the use of an adsorbent can be cited in particular. As an example of a chemical technique for eliminating the water formed during the synthesis, a desiccation agent can be cited in particular.

The water formed during the condensation reaction is advantageously eliminated by means of a desiccation agent chosen from the group comprised of the carbonates, the sulfates, calcium chloride, phosphorus pentoxide, the molecular sieves or combinations of these various desiccation agents. The desiccation agent can be introduced directly into the reaction medium.

According to a variant of the invention, the condensation reaction is carried out at atmospheric pressure and under an atmosphere of inert gas, such as argon or nitrogen.

According to another variant of the invention, the condensation reaction is carried out at reduced pressure.

According to an advantageous variant of the invention, at the end of the condensation reaction the mixture is brought to a lower temperature, from several degrees below the reaction temperature to 0° C., preferably to ambient temperature, and is taken up in a solvent capable of solubilizing the reducing alkyl-sugar monomer, in particular the alkyl-rhamnose, alkyl-fucose or alkyl-glucose monomer, with the aforementioned solvent being advantageously dichloromethane. The acid catalyst is neutralized using a weak base, preferably bicarbonate, for a period ranging from 1 minute to 24 hours, advantageously for 30 minutes.

According to the length of the chain, the products are purified either by column chromatography for the shortest chains, or by Soxhlet extraction for the other compounds. The two methods can be combined if very high purity is sought.

The principle of purification by Soxhlet extraction consists of mixing the crude reaction product (reducing alkyl-sugar, in particular alkyl-rhamnoside, alkyl-fucoside or alkyl-glucoside, residual alcohol, PTSA, reducing sugar, in particular rhamnose, fucose or glucose) with chromatography silica in a weight ratio near 1:4, and placing this mixture in a extraction cartridge: coupling a heated solid-liquid extraction method with a continuous chromatography method.

The weight yield of this process of synthesis of reducing alkyl-sugar monomers, in particular of alkyl-rhamnose, alkyl-fucose or alkyl-glucose monomers, is greater than 40%.

The medicament according to the invention is advantageously intended to regulate inflammatory mechanisms.

The medicament is in particular intended for the prevention or treatment of allergic, inflammatory or immune reactions or pathologies of the skin and/or mucous membranes. The medicament according to the invention is also intended to inhibit the immune response related to inflammatory stress.

The medicament according to the invention is in particular intended to inhibit the activation of leucocytes, such as human granulocytes, in particular human neutrophils and mast cells which prevent the release of the preformed mediators of the immune reaction. It also makes possible inhibition of the adhesion of circulating lymphocytes and endothelial cells, thus preventing the transmigration of these leucocytes to the inflammation site. It also makes possible inhibition, of the secretion of keratinocytic cytokines, activators of T lymphocytes and Langerhans cells such as IL-1 and TNF-$\alpha$, or of adhesion molecules such as ICAM-1 and VCAM, which contribute to the recruitment and trans-endothelial passage of leucocytes. The medicament according to the invention is also an inhibitor of the keratinocytic hyperplasia phenomenon.

The medicament according to the invention is also an inhibitor of antigen processing by the dendritic cells of the skin, of maturation of antigen-presenting cells, namely dermal dendritic cells and Langerhans cells, and of the recognition phenomenon between lymphocytes and antigen-presenting cells.

Thus, the medicament according to the invention is intended for the prevention or treatment of diseases chosen from the group comprised of atopic and/or contact eczema, inflammatory dermatoses, irritant dermatitis, acne, autoimmune diseases such as psoriasis, photo-immunosuppression, vitiligo, pityriasis, sclerodermas, rheumatoid arthritis, Crohn's disease and graft rejection.

The medicament according to the invention is also intended for the prevention and treatment of age-related chronic inflammatory problems and their consequences. The medicament is in particular intended for the prevention or treatment of diseases chosen from the group comprised of anaphylactic sensitivities, pigmentary anomalies of the skin, dermal hypervascularity and inflammatory fissuring.

According to a variant of the invention, the medicament is intended to reduce the allergenic and/or irritant character of a composition or perfume.

The medicament according to the invention advantageously contains from 0.001% to 50% by weight of reducing alkyl-sugars.

The medicament according to the present invention can be formulated for administration by any route. It is advantageously formulated to be administered by topical, oral, subcutaneous, injectable, rectal and vaginal routes.

When the medicament is formulated to be administered by oral route, the aforementioned medicament can appear in the form of an aqueous solution, an emulsion, tablets, gelatin capsules, capsules, powders, granules, solutions or oral suspensions.

When the medicament is formulated to be administered by subcutaneous route, the aforementioned medicament or the aforementioned composition can appear in the form of sterile injectable ampules.

When the medicament is formulated to be administered by rectal route, the aforementioned medicament can appear in the form of suppositories.

When the medicament is formulated to be administered by vaginal route, the aforementioned medicament can appear in the form of vaginal suppositories.

The medicament according to the invention is preferably a topical application. Thus, the medicament can be formulated so as to appear, for example, in the form of an aqueous solution, a white or colored cream, a pomade, a milk, a lotion, a gel, an ointment, a serum, a paste, a foam, an aerosol or a stick.

The quantity of the medicament according to the invention to be administered depends on the gravity and age of the ailment treated. Naturally, the doctor will also adapt the dosage according to the patient.

The present invention also relates to a method for the cosmetic treatment of skin and/or mucous membranes that are sensitive, irritated, intolerant, of an allergic tendency, aged, exhibiting danger signs, exhibiting a disorder of the cutaneous barrier, exhibiting cutaneous redness or exhibiting a non-pathological immunological imbalance related to intrinsic, extrinsic or hormonal aging, wherein it consists of applying to the skin and/or the mucous membranes a composition comprised of at least one reducing-sugar monomer whose hydroxyl function, advantageously the anomeric hydroxyl function, is substituted by an alkoxy radical at $C_2$-$C_{40}$, preferably at $C_2$-$C_{24}$.

The present invention also relates to a cosmetic treatment method to slow the natural aging of the skin and/or to prevent the accelerated aging of skin subjected to external attacks, in particular to prevent photo-induced aging of the skin, wherein it consists of applying to the skin a composition comprised of at least one reducing-sugar monomer whose hydroxyl function, advantageously the anomeric hydroxyl function, is substituted by an alkoxy radical at $C_2$-$C_{40}$, preferably at $C_2$-$C_{24}$.

The cosmetic composition applied in the cosmetic treatment method according to the invention advantageously contains from 0.001% to 50% by weight of reducing alkyl-sugars. The reducing sugar is advantageously selected from the group comprised of rhamnose, fucose and glucose.

The rhamnose, fucose or glucose can be of a levorotatory or dextrorotatory configuration. According to an advantageous variant of the invention, the rhamnose, fucose or glucose is of a levorotatory configuration.

The rhamnose, fucose or glucose can be in $\alpha$- or $\beta$-anomeric form. According to another advantageous variant of the invention, the rhamnose, fucose or glucose is in the $\alpha$-anomeric form.

According to an advantageous variant of the invention, the alkoxy radical includes from 5 to 12 carbon atoms, preferably 5 to 8 carbon atoms. According to an advantageous variant of the invention, $R_1$ represents a radical chosen from the group comprised of pentyl, octyl, decyl and undecyl.

Within the framework of the invention, the reducing alkyl-sugars can be prepared according to the process described previously or by any other process known to those skilled in the art.

When the cosmetic composition is formulated to be administered by topical route, the aforementioned composition can appear, for example, in the form of an aqueous solution, a white or colored cream, a pomade, a milk, a lotion, a gel, an ointment, a serum, a paste, a foam, an aerosol, a shampoo or a stick.

Other characteristics and advantages of the invention appear in the continuation of the description with the examples presented below. The following figures will be referred to in these examples. These figures and examples are intended to illustrate the present invention and cannot in any case be interpreted as limiting its scope.

FIG. 1: Viability of endothelial cells arising from peripheral lymphatic ganglia in the presence of rhamnose.

Figure 2:
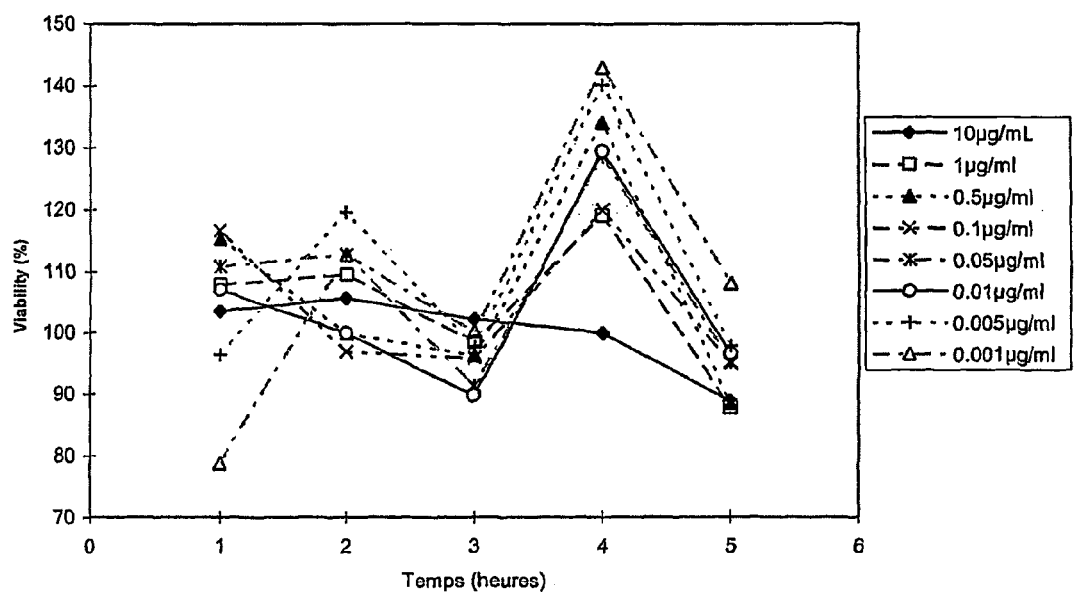

FIG. 2: Viability of endothelial cells arising from peripheral lymphatic ganglia in the presence of pentyl-rhamnoside.

EXAMPLE 1

Process of Synthesis of Dodecyl-Rhamnoside

Into a 100 ml two-neck round-bottom flask, surmounted with a condenser equipped with a desiccant ($CaCl_2$) trap, 2 g of rhamnose (1 equivalent) and 2 molar equivalents (4.6 g) of fatty alcohol (dodecyl alcohol) are introduced under argon.

0.1 molar equivalent of the acid catalyst p-toluenesulfonic acid (PTSA) is added to the preceding heterogeneous mixture maintained under argon. The medium is stirred (magnetic stirrer) at 70° C. for 3 hours.

After the reaction, the then homogeneous medium is cooled to ambient temperature. A solution of dichloromethane (20 ml) and a spatula-tip of $NaHCO_3$ are added to the mixture left stirring under argon. The medium is left thus for 30 minutes.

The solution is then filtered on paper. The filtrate (P2) containing the alkyl-rhamnosides is evaporated and concentrated in viscous oil.

Thus 1.9 g of P2 is recovered after filtration, and yield of 48% is achieved after a silica batch purification step.

The nature of the alkyl-rhamnosides is determined by NMR, HPLC and mass spectrometry.

Mass spectrometry is carried out by electrospray. These analyses reveal a maximum degree of polymerization of 2 for the polar head.

The 250 MHz NMR analyses are made in $CDCl_3$ or $D_2O$ on a Brucker AC250 multinuclear apparatus operating at 250.13 MHz for $^1H$.

The chromatographic analyses are carried out in reversed phase on a C18 grafted column (YMC-pack C18, 12 nm mean pore diameter, 5 µm particle diameter) and a LiChrospher 100 RP-8 column (125×4 mm internal diameter). The eluent selected is an acetonitrile-water (40-60) mixture, with a flow rate of 1.5 ml/min at 45° C. The detector is a Sedex 45 light-scattering detector.

These analyses make it possible to identify the alkyl-rhamnoside present in P2 as dodecyl-rhamnoside.

Pentyl-rhamnoside, octyl-rhamnoside, decyl-rhamnoside and undecyl-rhamnoside can be synthesized according to the same process by replacing dodecyl alcohol by pentyl alcohol, octyl alcohol, decyl alcohol and undecyl alcohol, respectively.

EXAMPLE 2

Reactivity of Sugars with Respect to Alcohol

In the case of short-chain linear alcohols, the reactivity of various sugars with respect to alcohol is good. Indeed, if two families of compounds, alkyl-rhamnosides and alkyl-glucosides, are considered, the results obtained for pentyl-saccharides are comparable. Alcohol, which is not very hydrophobic, ensures good contact by good wettability of the sugar and reactivity is thus increased. The yields obtained for the shorter-chain alcohols are always greater than 50%.

In the specific case of alcohols whose chain length is more than 8 carbons, the yields of alkyl-glucosides decrease very rapidly when the length of the hydrocarbon chain increases. Indeed, the alcohol becomes too hydrophobic and contact with the highly hydrophilic glucose is less and less assured.

This decrease in reactivity is much smaller in the case of rhamnose (see Table 1). The yields for the alkyl-rhamnosides are approximately 8 times higher than those of the alkyl-glucosides for the chain at $C_{12}$ and still nearly 6 times higher for the chain at $C_{16}$.

TABLE 1

Weight yields obtained after purification of alkyl-glucosides and β-alkyl-rhamnosides.

| | | | |
|---|---|---|---|
| Rh—$C_5$ | 50% | Glu-$C_5$ | 65% |
| Rh—$C_{12}$ | 47% | Glu-$C_{12}$ | 6% |
| Rh—$C_{16}$ | 27% | Glu-$C_{16}$ | 5% |

In Table 1, the abbreviation Rh represents rhamnose and the abbreviation Glu represents glucose. Thus, for example, Rh—$C_5$ represents pentyl-rhamnoside.

One of the suggested reasons explaining this reactivity is a greater hydrophobicity of the deoxy-sugars. Indeed, the elimination of the hydroxyl in position 6 and the presence of the methyl group make it possible to increase the hydrophobicity of the sugar.

The presence of the methyl group on the fifth carbon also makes it possible to increase the electron density of oxygen by a positive inductive effect and thus to stabilize the intermediate acting in the reaction mechanism. Rhamnose is thus more reactive than the hexoses with respect to fatty alcohols.

EXAMPLE 3

Physical Aspect of Alkyl-Rhamnosides as a Function of the Length of the Radical Alkyl Chain Alkyl-rhamnosides having linear chains at $C_5$, $C_6$, $C_8$, $C_{10}$, $C_{11}$, and oleyl are in viscous liquid form.

Alkyl-rhamnosides having linear chains at $C_{14}$, $C_{16}$, $C_{18}$ and $C_{22}$ are in solid form.

Alkyl-rhamnoside having a linear chain at $C_{12}$ is a highly compact gel.

EXAMPLE 4

Pharmacological Analysis of Alkyl-Rhamnosides

The various immune cells acting in these inflammation processes were studied. They are the dendritic cells of the skin, the endothelial cells, certain leucocytes and the keratinocytes.

1) Principles of Cellular Viability Measurement Techniques
   MTT [3-(4,5-dimethyldiazol-2-yl)-2,5-diphenyl tetrazolium bromide] reduction technique (sold by Sigma).

This technique corresponds to a colorimetric test allowing quantification of living, metabolically active cells in a non-radioactive manner. MTT is a cationic molecule which is bound to the membranes of mitochondria in a potential-dependant fashion. On the level of the mitochondria, MTT will be reduced to formazan blue by mitochondrial dehydrogenase. The living cells are thus colored blue, in contrast with the dead cells which remain transparent. The measure of viability is then carried out by measurement of the optical density using an automatic reader.

This method of analysis, however, seems to be better adapted for adherent cells (keratinocyte-type) than for non-adherent cells (monocytes and dendritic cells). Another study was thus envisaged to conclude on the cytotoxicity of the oligorhamnosides with respect to the differentiated cells analyzed, namely flow cytometry in the presence of propidium iodide.

XTT tetrazolium salt reduction technique.

This is a technique allowing quantification of cellular proliferation and of the number of living (metabolically active) cells, without the incorporation of radioactive isotopes. XTT, yellow in color, is a cationic molecule which is bound to the membranes of mitochondria in a potential-dependant fashion, as does MTT.

On the level of the mitochondria, XTT will be reduced to formazan (orange) by mitochondrial tetrazolium reductase. This method, more costly than the MTT method, does not require in its protocol the lysis of cells by SDS to release the dye. Indeed, the reduction product is soluble within the cell. The method is thus faster. Living cells, in the absence and presence of a treatment become colored, in contrast with dead cells which remain colorless. The level of formazan product is detected with the spectrophotometer at a wavelength of 450 nm and is directly proportional to the number of metabolically active cells.

2) Toxicity Tests

Keratinocytes were isolated and placed in culture from human skin biopsies arising from anonymous donors following a plastic surgery procedure. Measurements of optical density (absorbance) of the 4 wells treated with the same product concentration were averaged. This average was compared with the average of the measurements obtained for the 4 control wells (Student's t-test—comparison of means—significant difference at 95% if $p<0.05$ and 99% if $p<0.01$).

The viabilities of the treated cells are expressed as a percentage compared to the control (untreated cells) of 100% (OD treated/OD control×100).

Rhamnose does not exhibit cytotoxicity (see Table 2), even for the highest concentrations.

TABLE 2

Viability of keratinocytes in the presence of various rhamnose concentrations.

|  | Control | Rhamnose 1 mg/ml | Rhamnose 0.1 mg/ml | Rhamnose 0.01 mg/ml | Rhamnose 0.001 mg/ml |
|---|---|---|---|---|---|
| % viability | 100 | 104 | 98 | 100 | 95 |
| p (Student) |  | 0.504 | 0.679 | 0.991 | 0.407 |

Pentyl-rhamnoside exhibits cytotoxicity at concentrations greater than 2 mg/ml (see Table 3). This toxicity cannot be explained by an effect involving the break-down of fats by the alkyl-rhamnoside given that at a clearly higher concentration, near 70 g/l, no detergency effect was demonstrated during the studies on the phosphatidylcholine multilamellar vesicles.

TABLE 3

Viability of keratinocytes in the presence of various concentrations of pentyl-rhamnoside ($Rh-C_5$).

|  | Control | $Rh-C_5$ 5 mg/ml | $Rh-C_5$ 2 mg/ml | $Rh-C_5$ 1 mg/ml | $Rh-C_5$ 0.1 mg/ml |
|---|---|---|---|---|---|
| % viability | 100 | 40 | 53 | 74 | 94 |
| p (Student) |  | <0.01 | <0.01 | <0.01 | 0.145 |

Toxicity tests were also carried out with undecyl-rhamnose and octadecyl-rhamnose. The results are presented in Table 4 below:

TABLE 4

Viability of keratinocytes in the presence of various concentrations of $C_{11}$ and $C_{18}$ alkyl rhamnosides.

|  | Control | $Rh-C_{11}$ 500 µg/ml | $Rh-C_{11}$ 250 µg/ml | $Rh-C_{11}$ 100 µg/ml | $Rh-C_{11}$ 10 µg/ml |
|---|---|---|---|---|---|
| % viability | 100 | 30 | 11 | 17 | 81 |
| p (Student) |  | <0.01 | <0.01 | <0.01 | <0.01 |

|  | Control | $Rh-C_{18}$ 500 µg/ml | $Rh-C_{18}$ 250 µg/ml | $Rh-C_{18}$ 100 µg/ml | $Rh-C_{18}$ 10 µg/ml |
|---|---|---|---|---|---|
| % viability | 100 | 27 | 25 | 87 | 137 |
| p (Student) |  | <0.01 | <0.01 | <0.05 | 0.01 |

Endothelial cells were placed in culture, immortalized and stabilized in their phenotype. The cell lines studied were appendix endothelial cells, brain microvascular endothelial cells, mesenteric lymphatic ganglia endothelial cells, peripheral lymphatic ganglia endothelial cells and skin microvascular endothelial cells.

The cytotoxicity test was carried out by means of a biochemical test on the transformation of a tetrazolium salt, MTT. The results obtained are very positive, and no toxicity is demonstrated with pentyl-rhamnoside (see FIGS. 1 and 2). Viability is indeed always greater than 85%, and this is true for all of the cells lines studied.

FIG. 1: Viability of endothelial cells arising from peripheral lymphatic ganglia in the presence of rhamnose.

FIG. 2: Viability of endothelial cells arising from peripheral lymphatic ganglia in the presence of pentyl-rhamnoside.

Noted in particular is the appearance of a stimulation peak corresponding to 4 hours of incubation, which is the time necessary for the initiation of protein synthesis. The presence of this peak is interesting because it indicates that the cells tolerate the oligorhamnosides (absence of toxicity) and assimilate them. These products appear to enrich the culture medium.

These results are similar for the other endothelial cell lines.

3) Influence of Alkyl-Rhamnosides on Human Cells Cultivated in a Pro-Inflammatory Medium Assay of the $PGE_2$ released by the NHK stimulated by PMA.

Alkyl-rhamnosides were evaluated as an inhibiter of the release of $PGE_2$ in cellular supernatants. These products were placed in the presence of the NHK at the same time as the PMA at 1 ng/ml. Each condition tested was evaluated for stimulation on 4 wells of NHK.

The abbreviation NHK means normal human keratinocytes.

The abbreviation PMA means phorbol-12-myristate-13-acetate.

The results summarized in Table 5 below represent the mean $PGE_2$ concentration values (pg/ml), after 24 hours of treatment, given in each of the cellular supernatants, stimulated or not, and reported in a quantity of cells expressed in µg.

TABLE 5

Percentage of inhibition of the release of PGE$_2$ as a function of the concentration of alkyl-rhamnosides (Rh—C$_5$, Rh—C$_{11}$ and Rh—C$_{18}$).

|  | 1 mg/ml | 0.5 mg/ml | 0.1 mg/ml | 0.05 mg/ml | 0.02 mg/ml | 0.01 mg/ml |
|---|---|---|---|---|---|---|
| Rh—C$_5$ | 89% | 84% 63% | 64% | 61% | 29% | — |
| Rh—C$_{11}$ |  |  |  |  | 28% | 28% |
| Rh—C$_{18}$ |  |  |  |  | 2% |  |

Pentyl-rhamnoside exhibits a stronger inhibition (80% to 60%) for concentrations of 1 mg/ml to 0.05 mg/ml. Its activity decreases to 0.02 mg/ml: 29% inhibition.

Pentyl-rhamnoside exhibits a strong inhibition, from 60% to 80%, for concentrations ranging from 1 mg/ml to 50 μg/ml.

Undecyl-rhamnoside exhibits activity comparable to pentyl-rhamnoside in the range of 20 μg/ml, which confers to it comparable inflammatory activity.

4) Adhesion Between Endothelial Cells and Lymphocytes

The influence of alkyl-rhamnosides on adhesion between lymphocytes and not-activated endothelial cells, in particular the line of endothelial cells arising from the skin (HSkMEC), was evaluated. These cells were placed in the presence of a strong activator, TNF-α.

Adhesion is carried out in vitro under static conditions. The endothelial cells were cultured in wells in order to obtain a monolayer. The cells were pretreated for 5 hours in the presence or absence of alkyl-rhamnosides. As dodecyl-rhamnoside required a content of 0.1% by volume to be soluble in the culture media, a control containing 0.1% glycerol was also analyzed. Indeed, the 0.1% glycerol stimulated adhesion of the lymphocytes on HSkMEC (31%) whereas it did not have an effect on the other endothelial cell lines.

The suspension of labeled lymphocytes was at a concentration making it possible to obtain a ratio of 5 lymphocytes per endothelial cell. Adhesion was carried out for 30 minutes at ambient temperature. The label binds irreversibly to the lipids of the plasma membrane of the cells without affecting the biological properties of the membrane or cellular viability.

The adhesion of the lymphocytes on the endothelial cells was quantified by flow cytometry.

The first adhesion tests on the non-activated endothelial cell lines yields the following results. 1.1 mM pentyl-rhamnoside induces an increase in adhesion of lymphocytes on HPLNEC.B3 (37.9%) and a very strong increase in adhesion on HMLNEC compared to rhamnose (96.7%). It has an inhibiting effect on the adhesion of lymphocytes on HSkMEC of 37.3% compared to rhamnose. It has no effect or a very slight effect on HAPEC and HBrMEC.

1.5 mM dodecyl-rhamnoside decreases the adhesion of lymphocytes on HSkMEC by 34.2%. It increases adhesion on HAPEC by 44.1% and has no effect on HBrMEC, HPLNEC.B3 and HMLNEC.

The results of adhesion between lymphocytes and activated endothelial cells, summarized in Table 5 below, arise from groups of three adhesion tests.

TABLE 5

Results of adhesion between lymphocytes and endothelial cells (HSkMEC) in the presence of rhamnose derivatives.

|  | Medium | TNF | Control/TNF ratio |
|---|---|---|---|
| Control | 1.000 | 2.730 | 2.7 |
| Rhamnose | 1.630 | 2.450 | 1.5 |
| Pentyl-rhamnose | 1.900 | 3.100 | 1.6 |
| Glycerol control | 2.200 | 3.200 | 1.45 |
| Dodecyl-rhamnose | 3.200 | 1.900 | 0.59 |

The effect of 1.5 μM dodecyl-rhamnoside is confirmed on the endothelial cells with an inhibition of adhesion of 63%.

EXAMPLE 5

Evaluation of Cutaneous Irritant Potential of Pentyl-Rhamnoside on Reconstituted Epidermis The evaluation of cutaneous irritant potential on reconstituted epidermis is an alternative to animal experimentation. The principle is based on the evaluation of the irritant potential of the product tested by:

the study of cytotoxicity by quantification of the release of lactate dehydrogenase (LDH) and by reduction of MTT to tetrazolium salt, the study of inflammation markers by quantification of the release of interleukins IL$_{1\alpha}$ and IL$_8$.

The results are summarized in Table 6 below.

TABLE 6

Results of the evaluation of cutaneous irritant potential of pentyl-rhamnoside on reconstituted epidermis

|  |  | Rh—C$_5$ | 4% Triton |
|---|---|---|---|
| 24 hours of application | MTT % | 89.9 | 3.0 |
|  | LDH ratio | 1.4 | 124.7 |
|  | IL$_{1\alpha}$ ratio | 2.4 | 36.0 |
|  | IL$_8$ ratio | 5.2 | 3.7 |
| 72 hours of application | MTT % | 82.1 | 1.5 |
|  | LDH ratio | 1.0 | 77.3 |
|  | IL$_{1\alpha}$ ratio | 2.0 | 7.2 |
|  | IL$_8$ ratio | 4.0 | 0.9 |
| Classification |  | Mild irritant | irritant |

The results show that pentyl rhamnoside, at a concentration of 30%, is a mild irritant.

EXAMPLE 6

Study of the Sensitizing Capacity of Pentyl Rhamnoside by the LLNA Method

The abbreviation LLNA means local lymph node assay, which is an alternative method to experimentation using guinea-pigs for sensitizing capacity.

This test determines the sensitizing capacity of the test substance by measuring the proliferation of lymphocytes in auricular lymphatic ganglia. The proliferation of lymphocytes will be measured by determining the incorporation of tritiated methyl thymidine.

The results are summarized in Table 7 below.

TABLE 7

Results of the study of sensitizing capacity of pentyl-rhamnoside by the LLNA method.

| Concentrations studied | Solvent | Concentration 1: 3% | Concentration 2: 15% | Concentration 3: 30% | DNCB 0.25% dilution |
|---|---|---|---|---|---|
| DPM-BLANK | 13814.5 | 9921.5 | 8328.5 | 6378.5 | 125622.5 |
| DPM/Ganglion | 1726.8 | 1240.2 | 1041.1 | 797.3 | 15702.8 |
| RATIO | | 0.7 | 0.6 | 0.5 | 9.1 |
| Conclusion | | Not sensitizing | Not sensitizing | Not sensitizing | Sensitizing |

In Table 7, the abbreviation DPM means "disintegration per minute," the blank is the reference and DNCB means dinitrochlorobenzene, which serves as the sensitizing control.

The results show that pentyl-rhamnoside, even up to a concentration of 30%, is not sensitizing.

The invention claimed is:

1. A method for treating inflammatory diseases which comprises administering an effective amount of a reducing-sugar monomer of rhamnose or fucose, whose hydroxyl function is substituted by an $C_2$-$C_{40}$ alkoxy radical, as an active agent, to a patient in need thereof.

2. The method according to claim 1, wherein, in the reducing-sugar monomer, the substituted hydroxyl function is the anomeric hydroxyl function.

3. The method according to claim 1, wherein the alkoxy radical comprises from 5 to 12 carbon atoms.

4. The method according to claim 1, wherein the inflammatory disease is selected from the group consisting of allergic, inflammatory or immune reactions and pathologies of the skin and/or mucous membranes.

5. The method according to claim 1, wherein the inflammatory disease is due to an immune response related to inflammatory stress.

6. The method according to claim 1, wherein the inflammatory diseases is related to the activation of leucocytes, the secretion of keratinocytic cytokines, the keratinocytic hyperplasia phenomenon, antigen processing by the dendritic cells of the skin, the maturation of antigen-presenting cells and the recognition phenomenon between lymphocytes and antigen-presenting cells.

7. The method according to claim 1, wherein the inflammatory disease is selected from the group consisting of atopic and/or contact eczema, inflammatory dermatoses, irritant dermatitis, acne, autoimmune diseases such as psoriasis, photo-immunosuppression, vitiligo, pityriasis, sclerodermas, rheumatoid arthritis, Crohn's disease and graft rejection.

8. A method for treating age-related chronic inflammatory problems and their consequences which comprises administering an effective amount of a reducing-sugar monomer of rhamnose or fucose, whose hydroxyl function is substituted by an $C_2$-$C_{40}$ alkoxy radical, as an active agent, to a patient in need thereof.

9. The method according to claim 8, wherein the age-related chronic inflammatory problem is chosen from the group comprised of anaphylactic sensitivities, pigmentary anomalies of the skin, dermal hypervascularity and inflammatory fissuring.

10. A method for reducing the allergenic and/or irritant character of a composition or perfume which comprises administering an effective amount of a reducing-sugar monomer of rhamnose or fucose, whose hydroxyl function is substituted by an $C_2$-$C_{40}$ alkoxy radical, to a patient in need thereof.

11. The method according to claim 1, wherein the medicament contains from 0.001% to 50% by weight of the aforementioned reducing-sugar monomer.

12. The method according to claim 8, wherein the medicament contains from 0.001% to 50% by weight of the aforementioned reducing-sugar monomer.

13. The method according to claim 10, wherein the medicament contains from 0.001% to 50% by weight of the aforementioned reducing-sugar monomer.

14. A cosmetic treatment method to slow the accelerated aging of skin which is caused by photo-induced aging wherein it consists of applying to the skin a composition comprised of at least one reducing-sugar monomer of rhamnose or fucose whose hydroxyl function, is substituted by an alkoxy radical at $C_2$-$C_{40}$, as an active agent.

* * * * *